United States Patent [19]
Otterbacher et al.

[11] Patent Number: 4,746,754
[45] Date of Patent: May 24, 1988

[54] PREPARATION OF CARBONATE DIISOCYANATES AND RELATED COMPOUNDS

[75] Inventors: Eric W. Otterbacher; Abel Mendoza, both of Midland; Cynthia L. Rand, Sanford, all of Mich.

[73] Assignee: The Dow Chemical Company, Midland, Mich.

[21] Appl. No.: 864,062

[22] Filed: May 16, 1986

[51] Int. Cl.$^4$ .................. C07B 43/10; C07C 118/02; C07C 119/048

[52] U.S. Cl. ................................ 558/269; 558/273; 558/274; 558/282

[58] Field of Search ............... 558/269, 273, 274, 282

[56] References Cited

U.S. PATENT DOCUMENTS

| | | | |
|---|---|---|---|
| 3,078,294 | 2/1963 | Howe et al. | 260/453 |
| 3,124,607 | 3/1964 | Schisla | 260/463 |
| 3,162,664 | 12/1964 | Brotherton et al. | 260/463 |
| 3,218,347 | 11/1965 | Baker | 260/463 |
| 3,256,220 | 6/1966 | Brotherton et al. | 260/2.5 |
| 3,290,350 | 12/1966 | Hoover | 260/453 |
| 3,318,942 | 5/1967 | Brotherton et al. | 260/463 |
| 3,322,812 | 5/1967 | Brotherton et al. | 260/463 |
| 3,440,268 | 4/1969 | Stamm | 260/453 |
| 3,458,475 | 7/1969 | Krimm et al. | 260/47 |
| 3,488,376 | 1/1970 | Ulrich | 260/453 |
| 3,505,384 | 4/1970 | Krimm et al. | 260/463 |
| 3,654,338 | 4/1972 | Krimm et al. | 260/463 |
| 3,994,949 | 11/1976 | Meyer et al. | 260/453 P |
| 4,123,450 | 10/1978 | Weber, Jr. | 260/453 P |
| 4,128,569 | 12/1978 | Horn et al. | 260/453 PH |
| 4,130,577 | 12/1978 | Nagato et al. | 260/453 P |
| 4,361,513 | 11/1982 | Singh et al. | 260/453 P |
| 4,377,530 | 3/1983 | Trenbeath et al. | 260/453 P |
| 4,379,767 | 4/1983 | Alexanian et al. | 260/453 P |
| 4,395,369 | 7/1983 | Henderson, Jr. et al. | 260/453 P |
| 4,399,073 | 8/1983 | Schaefer | 260/453 P |
| 4,399,074 | 8/1983 | Schaefer | 260/453 P |
| 4,439,616 | 3/1984 | Singh et al. | 560/25 |

*Primary Examiner*—Donald B. Mayer
*Assistant Examiner*—Patricia M. Scott

[57] ABSTRACT

A class of novel tertiary alkyl isocyanates. Of these, novel carbonate diisocyanates can be prepared by contacting a carbonyl dihalide and an aminotertiaryalkylhydroxyaromatic compound in the presence of a base and a reaction medium under reaction conditions.

20 Claims, No Drawings

PREPARATION OF CARBONATE DIISOCYANATES AND RELATED COMPOUNDS

BACKGROUND OF THE INVENTION

The present invention relates to the preparation of isocyanates.

Organic isocyanates have many known uses and there are several known methods for their synthesis. Many methods are based on the knowledge that phosgene will react with active hydrogen-containing compounds. For example, U.S. Pat. No. 4,123,450 teaches the reaction of phosgene with phenol in the presence of NaOH in a two-phase reaction system to make phenyl chloroformate, which in turn is reacted with an alkylamine in a two-phase system to give the corresponding N-alkylcarbamate, which can be pyrolyzed to yield the alkyl isocyanate. U.S. Pat. No. 4,128,569 teaches the manufacture of isocyanates by reacting phosgene and a primary amine, including aromatic diamines having the divalent bridging groups —O—, —SO$_2$—, —CH$_2$—, and —C(CH$_3$)$_2$—. U.S. Pat. No. 3,440,268 teaches the production of isocyanates by reacting a primary amine with phosgene to form the corresponding carbamoyl chloride, and then heating the carbamoyl chloride to form the corresponding isocyanate plus hydrogen chloride. These methods do not employ an aminophenol in the preparation of isocyanates.

More specifically, organic isocyanates having the isocyanato moiety bonded to a tertiary alkyl carbon atom are especially useful, and several methods for their preparation are known. U.S. Pat. No. 3,290,350 teaches the preparation of tetramethylxylylene diisocyanates (hereinafter TMXDI's) by reacting isocyanic acid and certain vinylidene compounds, including aromatic vinylidene compounds. U.S. Pat. No. 4,377,530 teaches an improvement to the method of U.S. Pat. No. 3,290,350, using a high excess of the isocyanic acid. U.S. Pat. No. 4,361,518 teaches the production of TMXDI's by reacting the corresponding halides with an excess of isocyanic acid. Similarly, U.S. Pat. No. 4,379,767 teaches a two-step method for the preparation of TMXDI's. The method involves reacting an aromatic diisopropenyl compound with a carbamoyl halide to form the tertiary benzyl halide, which in turn is reacted with isocyanic acid to form the corresponding TMXDI. U.S. Pat. No. 4,395,369 teaches a similar method, and teaches that the aromatic moiety can contain —O—, —S—, —CO— and polymethylene linkages. U.S. Pat. Nos. 4,399,073 and 4,399,074 teach the production of TMXDI's by reacting alkali metal cyanates and t-alkylhalides under very specific reaction conditions. Thus, these known methods for producing TMXDI's require the use of cyanate salts or isocyanic acid and do not employ aminophenols. Isocyanic acid is hard to handle in that it tends to trimerize to form isocyanurates. Additionally, it is a severe explosion hazard. The reaction of organic halides with cyanate salts does not proceed readily except under very specific reaction conditions and with a limited number of catalysts.

U.S. Pat. No. 4,439,616 teaches a multistep process for the preparation of TMXDI's. The process involves preparing a carbamate from an olefin and, e.g., a carbamic acid alkyl ester in the presence of an acid catalyst. The acid catalyst is then completely neutralized, and the carbamate is then thermally cracked to form the corresponding TMXDI. Said method does not employ an aminophenol.

U.S. Pat. No. 3,488,376 teaches the phosgenation of a m- or p-aminophenol in an aprotic, polar solvent to give the corresponding m- or p-isocyanatophenol. In said process, only the amino moiety reacts with the phosgene.

In view of the deficiencies of the prior art methods, it would be desirable to provide a simple, one-step process for the preparation of aromatic alkyl diisocyanates, including especially useful novel aromatic tertiary alkyl polyisocyanates, which method would not require the use of cyanate moiety-containing reactants.

SUMMARY OF THE INVENTION

The process of the present invention is a process for the preparation of aromatic tertiary alkyl diisocyanates having at least one carbonate bridging moiety. One class of novel carbonate isocyanates can be prepared by the process of the present invention, i.e., by contacting an aminoalkylhydroxyaromatic compound with a carbonyl dihalide in the presence of a base and a reaction medium under reaction conditions such that a carbonate aromatic tertiary alkyl polyisocyanate is formed. The carbonate isocyanates of the present invention are unique in that they contain in the same compound at least one tertiary alkyl isocyanate moiety and at least one carbonate moiety. The invention further includes haloformate tertiary alkyl isocyanates.

Surprisingly, the process of the present invention for the first time allows the selective production of carbonate isocyanates in one step by the simultaneous reaction of a carbonyl dihalide with active hydroxyl and amino hydrogen atoms.

DETAILED DESCRIPTION OF THE INVENTION

The one-step process of the present invention advantageously employs an aminoalkylhydroxyaromatic compound, a carbonyl dihalide, a reaction medium and a base. The two-step process involves first preparing a novel haloformate isocyanate, and then contacting the haloformate isocyanate with an alkaline material and water or a polyhydroxyl compound to form a carbonate aromatic tertiary alkyl polyisocyanate.

The aminoalkylhydroxyaromatic compounds which can be employed for use in the process of the present invention are aromatic compounds having at least one hydroxyl moiety and at least one primary amino moiety wherein at least one of the amino moieties is attached to a tertiary alpha carbon atom. For the purposes of the present invention, the term "alpha carbon atom" refers to a carbon atom which is directly attached to a ring of an aromatic moiety of the aminoalkylhydroxyaromatic compound. Examples of typical aminoalkylhydroxyaromatic compounds include 2-amino-2-(4-hydroxyphenyl)propane, 2-amino-2-(3-hydroxyphenyl)propane, 2-amino-2-(2-hydroxyphenyl)butane, 2-amino-2-(4-hydroxyphenyl)-1,1,1,3,3,3-hexafluoropropane, 2-amino-2-(3,5-dimethyl-4-hydroxyphenyl)-1,1,1,3,3,3-hexafluoropropane, and the like. Preferred α-aminoalkylhydroxyaromatic compounds are represented generally by the formula:

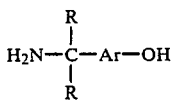

wherein Ar is a divalent aromatic moiety, and each R is independently lower alkyl, or aryl, with the proviso that two R moieties which are bonded to a common carbon atom can combine to form a cycloaliphatic ring. Especially preferred are α-aminoalkylphenols. Preferably, each R is methyl, and each Ar independently is represented by the formula:

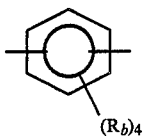

wherein each $R_b$ independently is H, lower alkyl, halo, lower alkoxy, aryl, aryloxy, —$COOR_d$ or —$OCOOR_d$, wherein each $R_d$ independently is aryl or lower alkyl. Each $R_b$ preferably is H. Most preferably, the hydroxyl moiety is in the para position relative to alkyl moiety. For the purposes of the present invention, the term "lower alkyl" refers to alkyl moieties having from 1 to about 6 carbon atoms, and includes substituted lower alkyl. For the purposes of the present invention, the terms "alkyl", "aliphatic", "aryl" and "aromatic" include inertly-substituted alkyl, inertly-substituted aliphatic, inertly-substituted aryl and inertly-substituted aromatic moieties. For purposes of the present invention, the term "inertly-substituted" refers to moieties having substituents which substantially do not interfere with the formation of carbonate isocyanates. Examples of inert substituents include moieties such as alkoxy, aryl, aryloxy, cyano, halo and the like.

The process of the present invention advantageously employs a carbonyl dihalide, which preferably is phosgene. The carbonyl dihalide may be gaseous or liquid, and may be diluted with gases which are inert under the reaction conditions. Examples of inert gases include nitrogen, carbon monoxide, and the like. The molar ratio of carbonyl dihalide to aminoalkylhydroxyaromatic compound typically ranges from about 1 to about 2, and preferably the ratio ranges from about 1.4 to about 1.6. Most preferably, a stoichiometric amount of carbonyl dihalide is employed, i.e., about 1.5 moles of carbonyl dihalide is employed per mole of aminoalkylhydroxyaromatic compound. Varying the ratio from the stoichiometric amount leads to excess carbonyl dihalide or lower conversion, and possibly leads to the formation of by-products, depending upon the rate of addition of the carbonyl dihalide.

A base is advantageously employed in the process of the present invention. The base scavenges the hydrogen halide, e.g., hydrogen chloride, which is formed in the reaction and which would otherwise be scavenged by the amino moiety of the aminoalkylhydroxyaromatic compound. Typical bases have a $pK_a$ in the range of from about 4 to about 11. Preferably, the base employed will have a $pK_a$ of from about 4.5 to about 7. Note that $pK_a$ values actually refer to the $pK_a$ of the conjugate acid of the base. For example, the conjugate acid of $NH_3$ is $NH_4^+$. Examples of typical bases include pyridine, N,N-dimethylaniline, N,N-diethylaniline, N-methylimidazole, sodium carbonate, sodium bicarbonate and the like. Primary and secondary amines typically should not be employed as the base in view of the fact that they could react with the carbonyl dihalide. Pyridine is the preferred base.

The process of the present invention is affected by the alkalinity or strength of the base. A weaker base, i.e., one with a relatively lower $pK_a$, generally will tend to produce haloformate tertiary alkyl isocyanates. A relatively stronger base will tend to produce a carbonate diisocyanate.

The base typically is employed in an amount sufficient to scavenge the hydrogen halide formed as the reaction proceeds. Commonly, from about 2 to 4 moles of base are employed per mole of aminoalkylhydroxyaromatic compound. Preferably, a stoichiometric amount of base is employed, i.e., about 3 moles of base are employed per mole of aminoalkylhydroxyaromatic compound. Increasing or decreasing this ratio leads to excess base or lower conversion, respectively.

A reaction medium is advantageously employed in the process of the present invention. The reaction medium functions to solubilize, at least partially, the reactants, the base, the intermediates and the products, and preferably should not interfere with the reaction of the present invention. Examples of suitable reaction media include chlorinated hydrocarbons, such as methylene chloride, perchloroethylene, chlorobenzene, dichlorobenzenes and the like; aromatic compounds, such as toluene, xylenes and the like; ethers, such as diethylether, diisopropyl ether and the like; esters, such as ethyl acetate, propyl acetate and the like; and alkanes, such as hexanes, heptanes and the like. These compounds can be used individually or as mixtures. Typically, from about 1 to about 20 parts by weight or more of reaction medium are employed per weight part of aminoalkylhydroxyaromatic compound.

The process of the present invention can be conducted at any combination of temperature and pressure at which a carbonate diisocyanate is produced. Typically, the contacting is conducted at a temperature of from about −20° C. to about 100° C. Preferably, the temperature is from about 0° C. to about 40° C.; most preferably the temperature is from about 10° C. to about 30° C. The typical process pressure ranges from about 50 to about 5000 kPa, absolute, with atmospheric pressure being preferred for the sake of convenience. The time required for the reaction varies according to the type and amount of reaction medium, the base, the reactants, the temperature, and the pressure employed. Typically the reaction takes from about 0.1 to about 100 hours.

When a carbonyl dihalide and an aminoalkylhydroxyaromatic compound are contacted under the reaction conditions described hereinabove, a novel carbonate diisocyanate is selectively produced. The carbonate diisocyanates of the present invention are diisocyanate compounds having at least one carbonate moiety. For the purposes of the present invention, the term "selectively" means that a carbonate diisocyanate is produced in a selectivity, as defined hereinbelow, of at least about 50 mole percent. In the process of the present invention it is desirable to selectively produce carbonate diisocyanates as opposed to ureas, carbamates, oligomers, and other theoretically possible by-products. Thus, for the purposes of the present invention, selectivity is defined as selectivity to a carbonate diisocyanate, and is calculated using the following equation: percent selectivity=100 (Y/X) wherein Y is twice the molar quantity of carbonate diisocyanate produced and wherein X is the molar quantity of aminoalkylhydroxyaromatic compound converted to anything. Advantageously, a selectivity of at least about 50 mole percent is achieved; preferably, the selectivity is at least about 70 mole percent. The carbonate diisocyanate product can be recovered by conventional means such as extraction or crystallization.

The aromatic tertiary alkyl isocyanates of the present invention include those isocyanates having at least one carbonate bridging moiety as well as haloformate tertiary alkyl isocyanates. Preferred isocyanates of the present invention can be represented generally by the formulas:

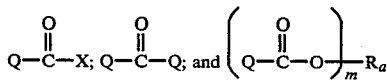

wherein for each formula, each Q is independently

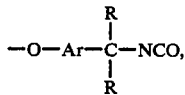

X is a halogen, m is an integer greater than 1, $R_a$ is a polyvalent moiety having a valence of m, and Ar and R are as defined hereinabove. $R_a$ preferably is a polyvalent hydrocarbon or inertly substituted polyvalent hydrocarbon moiety. More preferably, $R_a$ is a divalent aromatic moiety, such as, for example, a divalent moiety which is a remnant of benzene, naphthalene, biphenyl, 2,2'-bis(phenyl)propane, i.e., the hydrocarbon remnant of bisphenol A, and the like. For the purposes of the present invention the term "aromatic" includes groups having both aromatic and aliphatic moieties. Most preferably, $R_a$ is phenylene. X preferably is chloro. Preferably, m is from 2 to about 6. Most preferably, m is 2. Examples of typical carbonate diisocyanates include bis(4-(1-isocyanato-1-methylethyl)phenyl)carbonate, bis(3-(1-isocyanato-1-ethyl)phenyl)carbonate and the like. Preferred carbonate diisocyanates which can be prepared by the process of the present invention can be represented generally by the formula:

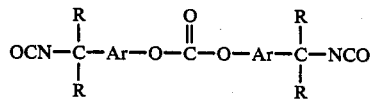

wherein R and Ar are as defined hereinabove. Compounds of this class can be produced by the process described hereinabove. The most preferred carbonate diisocyanates are represented generally by the formula:

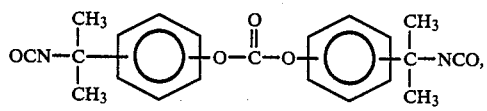

with the "para" positional isomer being most preferred.

Polyisocyanates of the general formula:

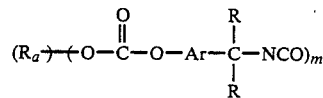

can be prepared by contacting a haloformate tertiary alkyl isocyanate, i.e., X=halo, as described herein, with a polyhydroxyl compound under the proper reaction conditions. The polyhydroxyl compounds are compounds which have at least two hydroxyl groups. Preferred polyhydroxyl compounds are represented generally by the formula:

wherein $R_a$ and m are as defined hereinabove. Examples of typical polyhydroxyl compounds include 1,4-butanediol, ethylene glycol, hydroquinone, pentaerythritol, 2,2-dimethyl-1,3-dihydroxypropane, sorbitol and the like. For examples of typical reaction conditions for the reaction of a hydroxyl-containing compound and a haloformate-containing compound, and for additional examples of polyhydroxyl compounds, see, e.g., U.S. Pat. No. 3,458,475, the teachings of which are incorporated herein by reference.

The haloformate tertiary alkyl isocyanates of the present invention, i.e., compounds wherein X is a halogen, can be prepared by contacting an α-aminotertiary-alkyl hydroxyaromatic compound, as described hereinabove, with a carbonyl dihalide, preferably phosgene, under reaction conditions such that a haloformate tertiary alkyl isocyanate is formed. These include reaction conditions which typically are employed for the reaction of amino alcohols and carbonyl dihalides. For example, see U.S. Pat. Nos. 3,458,475 and 3,654,338 regarding proper reaction conditions for the production of haloformate isocyanates. The teachings of said patents are incorporated herein by reference.

The haloformate tertiary alkyl isocyanate can be converted to a carbonate diisocyanate by contacting the haloformate t-alkyl isocyanate with water in the presence of an alkaline material. Preferably, the alkaline material will have a $pK_a$ which is at least as great as that of pyridine, i.e., it will have a $pK_a$ of at least about 5.2. A primary or secondary amine typically should not be employed as the alkaline material as these types of amines may react with the haloformate moiety. The reaction conditions for the reaction of water and haloformate t-alkyl isocyanate are similar to those for the reaction of haloformate t-alkyl isocyanate and polyhydroxyl compounds, as described hereinabove.

The α-aminoalkylphenols employed in the process of the present invention can be prepared by contacting an α-alkenylphenol and ammonia under reaction conditions sufficient to produce the corresponding α-aminoalkylphenol. The α-alkenylphenol is an ortho- or para-(α-alkenyl)phenol, having at least one α-alkenyl moiety. Examples of typical α-alkenylphenols include 1-(1-methylethenyl)-3-hydroxybenzene, 1-(1-methylethenyl)-2-hydroxybenzene, 1-(1-methylethenyl)-4-hydroxybenzene and the like. Typically, at least about one reactive equivalent of ammonia is employed per reactive equivalent of the α-alkenylphenol. Typically the amine is contacted with the α-alkenylphenol at a temperature of from about 0° C. to about 100° C. and at a pressure ranging between about 0 to about 1000 kPa, absolute. The contacting optionally can be conducted in the presence of a reaction medium. Examples of suitable reaction media include water, alcohols, ketones, phenols, ethers, and polar aprotic compounds. Typically, from about 0 to about 100 parts by weight of reaction medium are employed per weight part of α-alkenylphenol. The α-aminoalkylphenol product can be recovered by conventional means such as filtration or extraction.

SPECIFIC EMBODIMENTS

The following examples and preparations are given to illustrate the invention and should not be construed as limiting its scope. All parts and percentages are by weight unless otherwise indicated.

PREPARATION OF α-AMINOALKYLPHENOL

A 0.10-g sample of 4-(1-methylethenyl)phenol is exposed to excess, gaseous ammonia for about 1 day at 50° C. under autogenous pressure in a closed heavy wall glass bottle. The excess ammonia is purged and a quantitative yield of 2-amino-2-(4-hydroxyphenyl)propane is obtained.

EXAMPLE 1

To a stirred suspension of 10.2 g of 2-amino-2-(4-hydroxyphenyl)propane in 100 ml of methylene chloride containing 16.0 g of pyridine is added 10.0 g of phosgene at a temperature ranging from approximately 10° C. to 20° C. over a period of about 15 minutes. The reaction mixture is washed twice with 5 percent aqueous hydrochloric acid to remove pyridine, and then is washed twice with 5 percent aqueous sodium hydroxide. It is then washed once with water and once with a saturated solution of sodium chloride. The methylene chloride solution which results is dried over magnesium sulfate. Removal of the reaction medium gives 9.26 g of crude bis(4-(1-isocyanato-1-methylethyl)phenyl)carbonate. Recrystallization from hexane gives pure, white, crystalline bis(4-(1-isocyanato-1-methylethyl)phenyl)carbonate (hereinafter called CDI) having a melting point of 78° C. The structure is confirmed by infrared spectroscopy, proton nuclear magnetic resonance spectroscopy, $^{13}$C nuclear magnetic resonance spectroscopy, and mass spectroscopy.

Example 1 demonstrates a one-step process for the preparation of a carbonate diisocyanate from an α-aminoalkylphenol.

EXAMPLE 2

One equivalent of triethylamine is substituted for pyridine in Example 1. The results of the experiment are virtually identical.

EXAMPLE 3

One equivalent of N-methylimidazole is substituted for pyridine in Example 1. The results of the experiment are virtually identical.

Examples 2 and 3 demonstrate processes which employ bases other than pyridine.

EXAMPLE 4

Thirty grams of 4-(1-amino-1-methylethyl)phenol is slurried in diethylaniline (90 g) and added dropwise (2-5 ml/min) with a peristaltic pump to a solution of phosgene (60 g) in methylene chloride (200 ml) at a temperature of about 0° C. to about 20° C. The phosgenation is complete within about ½ hour after the addition of the aminophenol. The solvent and excess phosgene are removed under vacuum to leave a mixture of amine salts (white solid) and a chloroformate isocyanate (4-(1-isocyanato-1-methylethyl)phenyl)chloroformate). The product is extracted from the salts with hexane/CH$_2$Cl$_2$ (90:10 mixture).

The chloroformate isocyanate solution is washed with 6N HCl (200 ml) to remove residual amines and is sequentially washed with neutral water and saturated NaHCO$_3$. After drying over MgSO$_4$ and concentration in vacuo 42.18 g (90 percent pure by capillary gas chromatography) of the chloroformate isocyanate is obtained. Distillation at 0.5 mm Hg gives the product in 73 percent yield and >97 percent purity. The spectral data are in accord with its structure, and are as follows: $^1$H NMR (δ); 1.7 (Me, S) 7-7.7 (Ar, AA'BB'); IR (cm$^1$); 2232 (NCO, strong), 1760 (chloroformate, strong); GC-MS; parent ion 239 (percent RA, 3.87), 224 (percent RA, 71.12), 225 (percent RA, 7.89), 226 (percent RA, 23.78), 227 (percent RA, 2.24); and $^{13}$C NMR (ppm); 150.34, 149.66, 145.35, 126.39, 120.65, 60.61, and 32.15. The NCO carbon is not discernible by $^{13}$C NMR.

Example 4 demonstrates the preparation of a chloroformate isocyanate from an α-aminoalkylphenol.

EXAMPLE 5

The chloroformate isocyanate of Example 4 (23.9 g, 0.10 mole) is dissolved in ethyl acetate (50 ml) and is cooled to 10° C. with an ice bath. Water (0.9 g, 0.05 mole) is added to this solution. Droplets are visible in the bottom of the reactor. Pyridine (8 g, 0.1 mol) in ethyl acetate (50 ml) is added dropwise to the solution of chloroformate and water. Initially a yellow colored complex of pyridine chloroformate develops but dissipates as the reaction proceeds to give the product and pyridine HCl. The product can be isolated by pouring into dilute HCl (1-2N) and extracting with hexane. A NaHCO$_3$ wash gives 22 g of crude material. After drying in vacuo, CDI is obtained in 88 percent yield. The spectral and physical properties of this material are in accord with its structure: $^1$H NMR (CDCl$_3$) δ 1.74 (s, 6H methyl), 7.2 to 7.6 (4A'BB': 8H aromatic) ppm; $^{13}$C NMR (CDCl$_3$) δ 33.17, 60.52, 120.95, 125.98, 144.25, 150.23, 152.10 ppm. The isocyanate carbon does not appear in the $^{13}$C NMR; however, IR clearly shows the NCO band at 2256 wave numbers. Hydrolyzable chloride levels are titrated by the standard ASTM method at 16.7 ppm. Weight percent purity (by ASTM D 1638 74 titration for NCO) is 100 percent.

Example 5 demonstrates the preparation of a carbonate diisocyanate from a chloroformate isocyanate. The procedures of Examples 4 and 5 demonstrate a two-step reaction sequence for the preparation of carbonate diisocyanates from α-aminoalkylphenols. Thus, Examples 4 and 5 demonstrate that a chloroformate isocyanate can be directly converted to the carbonate diisocyanate in the same reaction vessel, or that it can be isolated and subsequently converted to the carbonate diisocyanate in a second step in the presence of water and an alkaline material. However, as demonstrated in Examples 1-3, the preferred process is the one-step procedure since, surprisingly, this one-step process for the first time allows the selective production of carbonate isocyanates by the simultaneous reaction of a carbonyl dihalide with active hydroxyl and amino hydrogen atoms.

EXAMPLE 6

The chloroformate isocyanate of Example 2 (2.4 g) is dissolved in ethyl acetate (25 ml) and vigorously stirred with an aqueous solution of excess $NaHCO_3$. The major product is CDI. The layers are separated and the ethyl acetate dried over $MgSO_4$. Concentration in vacuo gives 1.14 g of CDI with consistent spectral properties.

Example 6 demonstrates the use of a base other than pyridine in the process of Example 5.

EXAMPLE 7

N-methylimidazole (0.82 g) in $CH_3CN$ (10 ml) is added to the chloroformate isocyanate of Example 4 (2.39 g) in acetonitrile (10 ml) at room temperature. The reaction is stirred under $N_2$ for ½ hour. Hydroquinone (0.55 g) is dissolved in 10 ml of acetonitrile and added to the chloroformate-imidazole complex. After stirring for ½ hour the reaction mixture is poured into water and extracted with ethyl acetate. The organic phase is washed first with dilute HCl and then with saturated $NaHCO_3$. The organics are dried over $MgSO_4$ and concentrated in vacuo give quantitative yield of a white solid. This material is taken up in 200 ml hot hexane and enough ethyl acetate is added to solubilize all materials. The solution is hot filtered, slightly concentrated and allowed to cool slowly. After recovery and drying, 1.51 g of white crystalline material is obtained. Spectral data is consistent with the compound's structure:

$^1$H NMR ($CDCl_3$) δ 1.72 (s, 1H methyl), and 7.05–7.75 (m, 12H aromatics) ppm.

$^{13}$C NMR ($CDCl_3$) δ 38.14, 60.52, 120, 92, 122.13, 126.01, 144.32, 148.88, 150.14 and 151.99 ppm.

m.p. 125°–128° C.

Elemental analysis calculated: 65.11 percent C, 4.68 percent H, 5.42 percent N. Found: 65.1 percent C, 4.79 percent H, 5.37 percent N.

Example 7 demonstrates the preparation of a dicarbonate diisocyanate from a polyhydroxyl compound and a chloroformate isocyanate.

What is claimed is:

1. A tertiary alkyl isocyanate compound selected from $$Q-\overset{O}{\underset{\|}{C}}-X;$$

$$Q-\overset{O}{\underset{\|}{C}}-Q; \text{ or}$$

$$\left(Q-\overset{O}{\underset{\|}{C}}-O\right)_m R_a$$

wherein m is at least 2, X is a halogen, $R_a$ is an inertly substituted or unsubstituted polyvalent hydrocarbon moiety, and each Q independently is a moiety of the formula:

$$OCN-\overset{R}{\underset{R}{C}}-Ar-O-$$

wherein each R independently is aryl or lower alkyl, with the proviso that two R moieties which are bonded to a common carbon atom can combine to form a cycloaliphatic ring, and each Ar independently is a divalent aromatic moiety.

2. The compound of claim 1 of the formula:

$$\left(Q-\overset{O}{\underset{\|}{C}}-O\right)_m R_a$$

wherein $R_a$ is a divalent aromatic moiety.

3. The compound of claim 2 wherein m is from 2 to about 6.

4. The compound of claim 3 wherein $R_a$ is phenylene.

5. The compound of claim 4 wherein each R is lower alkyl.

6. The compound of claim 5 wherein each R is methyl.

7. The compound of claim 1 of the formula:

$$Q-\overset{O}{\underset{\|}{C}}-X$$

wherein X is chloro.

8. The compound of claim 7 wherein each R is methyl and Ar is phenylene.

9. The compound of claim 1 comprising a carbonate tertiary alkyl diisocyanate of the formula:

$$OCN-\overset{R}{\underset{R}{C}}-Ar-O-\overset{O}{\underset{\|}{C}}-O-Ar-\overset{R}{\underset{R}{C}}-NCO.$$

10. The compound of claim 9 wherein each Ar independently is represented by the formula

[benzene ring with $(R_b)_4$ substituents and two bonds]

wherein each $R_b$ independently is H, lower alkyl, halo, lower alkoxy, aryl, aryloxy, $-COOR_d$ or $-OCOOR_d$, wherein each $R_d$ independently is aryl or lower alkyl.

11. The compound of claim 9 wherein each R is methyl.

12. The compound of claim 10 wherein each R is methyl.

13. The compound of claim 12 wherein each $R_b$ is H.

14. A process comprising contacting an α-aminotertiaryalkylhydroxyaromatic compound with a carbonyl dihalide in the presence of a base and a reaction medium under reaction conditions such that a carbonate diisocyanate is formed.

15. The process of claim 14 wherein the conjugate acid of the base has a pK$_a$ of from about 4 to about 11.

16. The process of claim 14 wherein the aminoalkylhydroxyaromatic compound is represented by the formula:

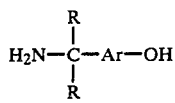

wherein Ar is a divalent aromatic moiety, and each R is independently H, lower alkyl, or aryl, with the proviso that R moieties which are bonded to a common carbon atom can combine to form a cycloaliphatic ring.

17. The process of claim 16 wherein each Ar independently is represented by the formula

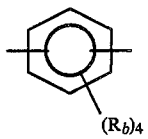

wherein each R$_b$ independently is H, lower alkyl, halo, lower alkoxy, aryl, aryloxy, —COOR$_d$ or —OCOOR$_d$, wherein each R$_d$ is independently is aryl or lower alkyl, and wherein each R is independently lower alkyl.

18. The process of claim 17 wherein each R is methyl.

19. A process comprising contacting phosgene and an α-aminoalkylphenol represented by the formula:

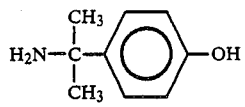

in the presence of pyridine and a halogenated hydrocarbon reaction medium under reaction conditions such that there is formed a diisocyanate having the formula:

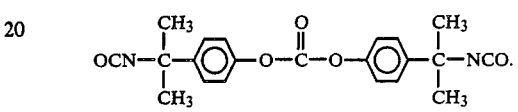

20. The process of claim 19 wherein the reaction medium is methylene chloride.

* * * * *